United States Patent [19]

Chambers

[11] 4,274,166
[45] Jun. 23, 1981

[54] SOCKET OR CAST BRIM

[76] Inventor: Gary R. Chambers, 705 McFarland St., Morristown, Tenn. 37814

[21] Appl. No.: 35,461

[22] Filed: May 3, 1979

[51] Int. Cl.³ .................................................. A61F 1/02
[52] U.S. Cl. ........................................ 3/17 R; 128/90
[58] Field of Search .................... 128/80 R, 85, 87 R, 128/90, 83, 91 R; 3/17 R, 19, 17 SS, 18, 20, 2

[56] References Cited

U.S. PATENT DOCUMENTS

| | | | |
|---|---|---|---|
| 383,569 | 5/1888 | Gault | 3/18 |
| 457,823 | 8/1891 | Rounds | 3/17 R |
| 1,497,219 | 6/1924 | Martino | 3/19 |
| 2,594,751 | 4/1952 | Fahlstrom | 3/17 R |
| 2,671,225 | 3/1954 | Schoene et al. | 3/19 |
| 2,800,129 | 7/1957 | VanSwaay | 128/90 |
| 2,808,593 | 10/1957 | Anderson | 3/17 R |
| 2,908,016 | 10/1959 | Botko | 3/17 R |
| 3,545,009 | 12/1970 | Colley | 3/17 SS |
| 3,784,988 | 1/1974 | Trumpler | 3/18 |

FOREIGN PATENT DOCUMENTS

| | | | |
|---|---|---|---|
| 2054922 | 5/1971 | France | 128/90 |
| 1233172 | 5/1971 | United Kingdom | 128/90 |

*Primary Examiner*—Clifford D. Crowder
*Attorney, Agent, or Firm*—Pitts & Kesterson

[57] ABSTRACT

A quadrilateral or thigh brim suitable for use as a socket brim for an amputee or with a cast brace for patients with a leg fracture is disclosed. The brim is molded as a sleeve having a modified rectangular cross-section which substantially conforms to the cross-section of a human thigh and is made of a resilient material such as a polyethelene foam material in such a manner that it provides both cushioning and a semirigid structure. The sleeve further includes contact surfaces which are rolled or tear drop shaped edges around the top area which will contact the buttocks and groin area to reduce and eliminate irritations due to chaffing, etc. In use, the brim size is selected such that it can be moved up over the leg into a slightly snug fit which will not interfere with blood circulation. When used for a fracture or the like, the plaster or other cast bracing material is then wrapped or otherwise molded to the leg over the brim resulting in a cast and brim combination which provides a rigid cast structure for the fracture and a cushioned and nonchaffing brim for the thigh. In a similar manner, for an amputee, the brim is moved into place and then the prosthetic device is molded to the brim thereby providing cushioning or padding to the thigh.

6 Claims, 6 Drawing Figures

SOCKET OR CAST BRIM

BACKGROUND OF THE INVENTION

The present invention relates to a quadrilateral or upper thigh brim in general and more particularly to such a brim molded of a resilient material in such a manner that it provides both cushioning and a semirigid structure. The treatment of fractures throughout history has ranged from simple splints to the modern cast wrapped plaster and other materials in use today. Although modern casts have eliminated some of the uncomfortableness which is always associated with a broken limb, casts which must extend around the upper thigh and contact the groin and buttock areas are particularly uncomfortable due to the chaffing of the upper leg area from the top edge of the rigid cast. To help reduce the uncomfortableness of such upper leg casts, semirigid polyethelene or plastic brims are typically used by physicians in treating fractures which require a cast over the thigh area. The polyethelene or plastic materials from which these brims are made have some flexibility, but are typically hard and do not yield to direct pressure on the material. These prior art brims are typically of a split sleeve nature to accomodate the different size and/or shape of an upper thigh. Such a split is necessary for different size cross-sections of a leg. This is because although the plastic material may be flexible, it has substantially no ability to stretch or yield to pressure. Although the prior art brim often uses a rolled edge to help eliminate some of the irritation to the upper thigh area, unfortunately, the rolled edges although helpful still do not eliminate the chaffing and irritation in the buttock and groin area. Therefore, it would be desirable to provide a brim for the upper thigh which provides both cushioning and padding, can accomodate some variation due to the different sizes of thighs, and which provides a strong semirigid support to which the plaster cast or prosthetic device can be molded.

Therefore, it is a object of this invention to provide a thigh brim which is simple and inexpensive to manufacture.

It is another object of this invention to provide a thigh brim which is resilient and which provides cushioning and padding when used.

It is yet another object of this invention to provide a thigh brim which can be used as a socket brim for an amputee or as a cast brace brim for treating fractures.

It is also an object of this invention to provide a thigh brim having both cushioning and a semirigid structure.

SUMMARY OF THE INVENTION

To accomplish the above mentioned objects as well as other objects which will become evident from the following drawings and detailed description, the present invention provides a quadrilateral or thigh brim suitable for use as a socket brim for application of immediate fit prosthesis after amputations with a cast brace for treating patients with fractures. The brim comprises a sleeve made of a resilient material having a cross-section suitable for conforming to the thigh of a patient being treated. The sleeve includes a front portion and an outside thigh portion having substantially straight sides of first selected heights, and a back portion and inside thigh portion of second selected heights which are less than the heights of the front portion and outside thigh portion. The top edges of the back portion and the inside thigh portion include a contact surface which is integrally molded to such sides for providing support and cushioning to the buttocks and groin area. The brim is molded from a resilient material such that the front, back, inside thigh, outside thigh portions and the contact surfaces all provide a cushioned yet semirigid structure. Accordingly, the above mentioned objects and subsequent description will be more readily understood by reference to the following drawings wherein:

DESCRIPTION OF THE INVENTION

Figure 1:
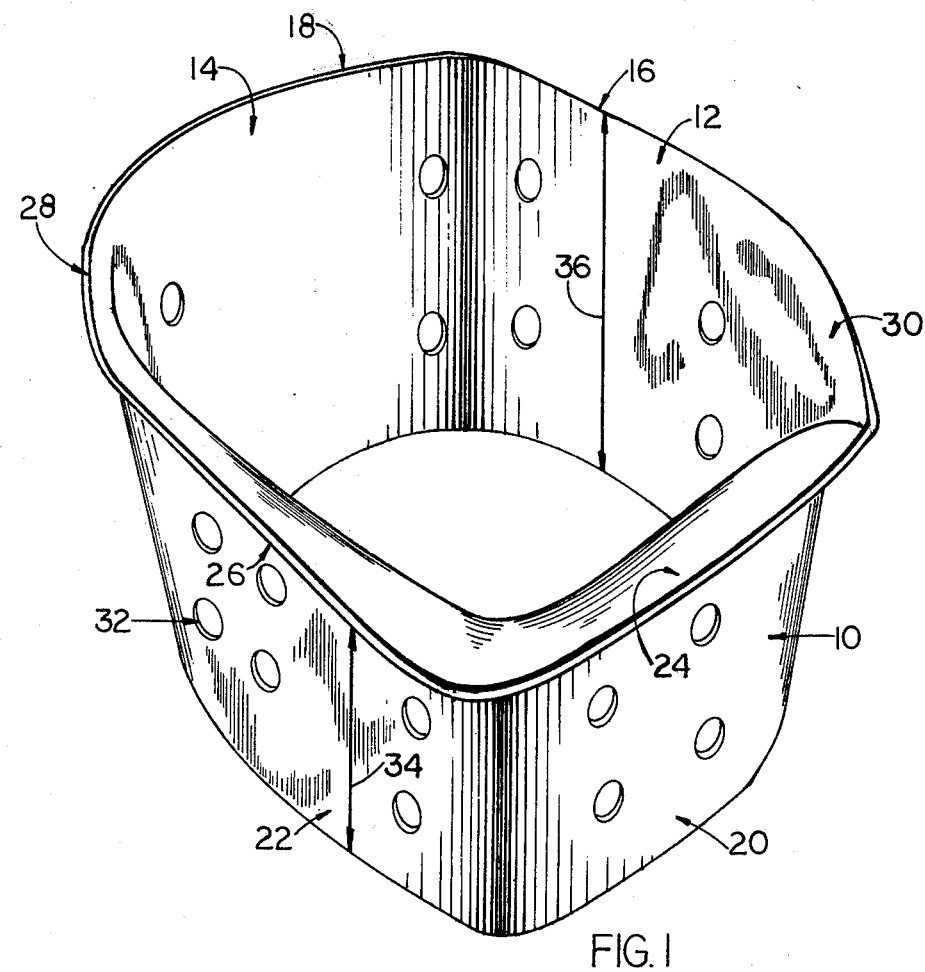
FIG. 1 is a perspective view of a thigh brim viewed from the back and illustrating various features of the invention.

Referring now to FIG. 1 there is shown a quadrilateral or thigh brim incorporating the features of this invention. From the drawing, which is a perspective view looking at the back of a brim for a left leg, it can be seen that the brim is basically a sleeve structure 10 having substantially rectangular cross-section area which will substantially conform to the cross-section of the human thigh. The substantially rectangular cross-section is desirable in that it controls, that is, reduces or eliminates the possibility of the brim rotating around the leg during use. In addition, it provides weight bearing support to the ischial or pelvic area. Although the illustrated brim is for the left leg, it will be appreciated that a brim for the right leg would be substantially a mirror image of the illustrated brim. The front side or portion 12 of the brim and the outside of the leg or left portion 14 of the brim of FIG. 1 have straight sides which may come to a feathered edge 16 and 18 respectively. The right side 20 of the brim which contacts the groin area and the back side of the brim 22 of the brim which contacts the buttocks area have enlarged contact surfaces 24 and 26 respectively which are a rolled or substantially tear drop shape to help eliminate or reduce irritation due to chaffing while at the same time providing both cushioning and additional support. Thus, the left rear corners 28 and right front corner 30 are molded such that they make a transition from the straight edges 16 and 18 to the rolled and tear drop shaped edges 24 and 26. Also shown, are a multiplicity of holes such as illustrated by the reference number 32 which allows breathing or air circulation of the brim as well as providing indentations for strengthening the bond between the plaster or prosthetic device and the brim itself.

Figure 2:
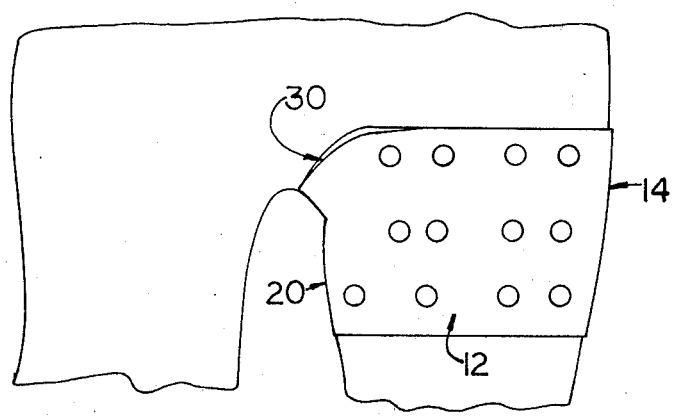
FIG. 2 is a front elevation view of the brim illustrated in FIG. 1 in place on the patient.

Referring now to FIG. 2, there is shown an elevation front view of the brim of this inveniton in place on a patient prior to the cast brace or prosthetic device being molded into place.

Figure 3:
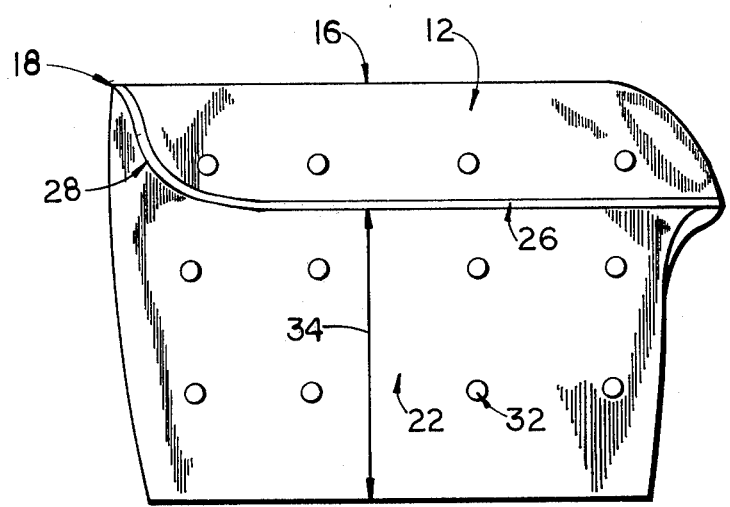
FIG. 3 is a rear elevation view of the brim shown in the FIG. 1.
Figure 4:
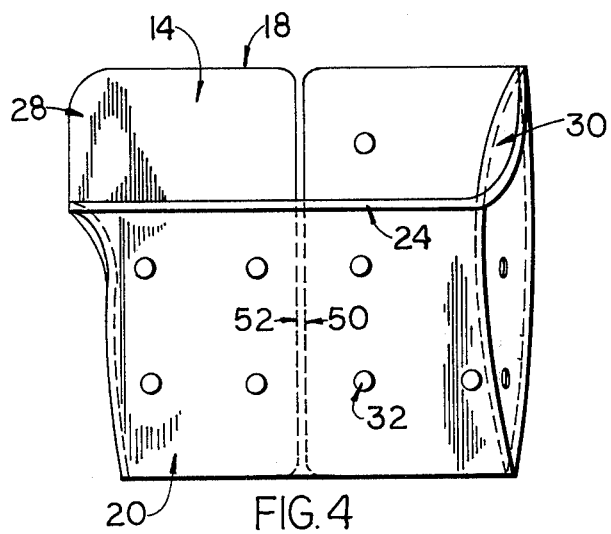
FIG. 4 is a right side elevation view of the brim shown in FIG. 1 modified to show a split sleeve embodiment.
Figure 5:
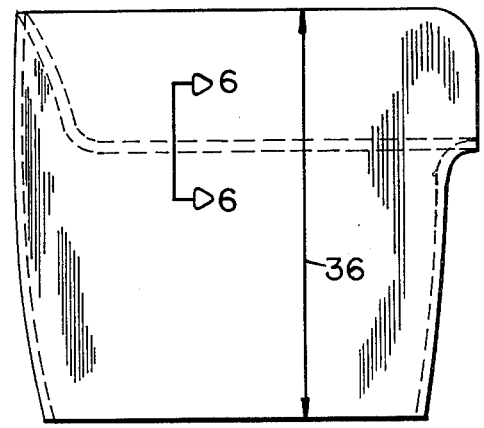
FIG. 5 is a left side elevation view of the brim shown in FIG. 1 showing an alternate embodiment of the invention in that the breathing holes have been deleted.

As can be more clearly seen in FIG. 3 which shows a back elevation view of the brim of this invention, the height of side 22 as represented by arrow 34, is significantly less than the height of side 12 as represented by arrow 36 of FIG. 1. Thus, it will be appreciated that the rolled edge 26, attached or molded to shorter side 22 provides room for protrusion of the buttocks and a rounded and cushioned surface area for the lower part of the buttocks. In a like manner, side 20 of the brim which is in contact with the groin area is shorter than side 14 of the brim which is on the outside of the upper thigh. FIG. 4, which is a right side elevation view of the brim as shown in FIG. 1, more clearly portrays the short side 20 and the high side 14 which is on the outside of the upper thigh. It should also be understood that although the brim as illustrated in the drawings is rather short and only extends a short distance down the leg, in some applications it may be desirable for the brim to extend all the way down the leg of a patient to a location just above the knee. Such a brim is particularly useful for providing a smooth surface and cushioning as well as a form for those applications where plaster or other cast bracing material is to be molded to the leg. The illustration of FIG. 4 also shows an alternate embodiment of the invention wherein the brim has been split for certain applications. FIG. 5 which is a left side view (i.e. viewing from the outside of the upper thigh) of the brim shown in FIG. 1 is an alternate embodiment of the invention in that the breathing or air circulation holes 32 have been deleted.

Figure 6:
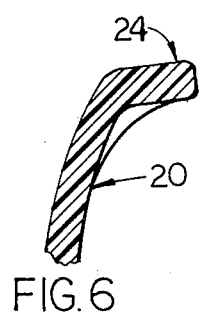
FIG. 6 is a transversectional view of the upper brim edge which contacts the buttocks and groin area showing that the brim lip has a tear shape cross-section for support and cushioning.

Referring now to FIG. 6, there is a transversectional view of the contact surfaces 24 and/or 26 such as is in place on the top edge of short sides 20 and 22. As can be seen from this figure, the cross-section of contact surfaces 24 and 26 have an enlarged cross-section thereby providing increased cushioning and support, while at the same time removing the sharper edges which are most inclined to cause irritation due to chaffing. The brim is made of a resilient or cushioning type material such as a polyethylene or polyurethane foam material, and is formed in such a manner and to such a thickness which may vary between about one quarter inch to one inch, such that it can provide both the cushioning inherent in such a foam material and such that it further provides the desirable semirigid structure. Materials particularly suitable for this purpose include Plastazoam™ manufactured by United States Manufacturing Company of Pasadena, California. Thus, it will be appreciated that because of the flexability of the material the brim can be premolded to a few selected sizes so that one of the selected sizes can cover a range of different sized individually. Therefore, for a particular range of individuals there is a universal size.

Therefore, as an example to use the brim of this invention for a fracture, a brim of substantially the proper cross-sectional area is selected by the physician and slid over the foot and upper leg to the upper thigh. The brim is then rotated until it is properly located and snugly fits the buttock and groin area of the patient, and as was mentioned heretofore the substantially rectangular shape helps maintain the brim in the proper position. Once in place, the plaster wrap or other cast material is molded to the lower portion of the brim and then around the leg as necessary and as determined by the physician to provide the desired support and immobility. In the embodiment shown in FIG. 4, which incorporates the split side, the brim can be placed on the patient by prying the edges 50 and 52 apart, and moving the brim onto the patients leg at the desired location. The memory of the material will substantially close the split and the cast can then be molded about the brim. As necessary or desired, a suitable strap such as Velcro can be used to close the slit.

Thus, although the present invention has been described with respect to specific embodiments of brims for upper thighs for use with cast braces and prosthetic devices, it is not intended that such specific references be considered limitations upon the scope of this invention except insofar as is set forth in the following claims:

What is claimed is:

1. A semi-rigid upper thigh brim suitable for use with a cast for treating fractures comprising:
   a sleeve having top and bottom edges and having a preselected cross-section corresponding to the cross-section of the upper thigh of a human being, said sleeve for fitting around the upper thigh of a patient and being made of a resilient material suitable for conforming substantially to the upper thigh of said patient, said sleeve including a front and outside thigh portion having substantially straight sides of a first selected length, and each of said front and outside straight sides having feathered top edges, and a back portion and inside thigh portion of a second selected length, which second selected length is less than said first selected length, said sleeve being suitable for bonding thereto a pliable cast material which subsequently cures to a hard and rigid material suitable for bracing and immobilizing a fracture and said sleeve defining a multiplicity of apertures to receive said pliable cast material to strengthen said bond; and
   contact surfaces integrally moded to said top edges of said back portion and said inside thigh portion of said sleeve and shaped to form a smooth transistion from said feathered top edges of said front and outside portions and to provide padding and support to the buttocks and groin areas of said patient, said front, back inside thigh, outside thigh portions and said contact surfaces being molded with a thickness such that said brim provides both cushioning and a semirigid structure between said cast and said patient.

2. A semirigid upper thigh brim suitable for use as a socket brim for prosthetic devices used by amputees comprising:
   A sleeve having top and bottom edges and having a preselected cross-section corresponding to the cross-section of the upper thigh of a human being, said sleeve for fitting around the upper thigh of a patient and being made of a resilient material suitable for conforming substantially to the upper thigh of said patient, said sleeve including a front and outside thigh portion having substantially straight sides of a first selected length and each of said front and outside straight sides having feathered top edges, and a back portion and inside thigh portion of a second selected length, which second selected length is less than said first selected length, said sleeve being suitable for bonding thereto a pliable material for molding into a prosthetic device for an amputee, which pliable material subsequently transforms into a rigid prosthetic device and said sleeve defining a multiplicity of apertures to receive said pliable material to strengthen said bond; and contact surfaces integrally molded to said top edges of said back portion and said inside thigh portion of said sleeve and shaped to form a smooth transistion from said feathered top edges of said front and outside portions and to provide padding and support to the buttocks and groin areas of said patient, said front, back, inside thigh, outside thigh portions and said contact surface being molded with a thickness such that said brim provides both cushioning and a semirigid structure between said rigid prosthetic device and said patient.

3. The apparatus of claim 1 or 2 wherein said sleeve has substantially a rectangular cross-section for controlling rotation of said brim and for providing ischial weight bearing support.

4. The apparatus of claims 1 or 2 wherein said sleeve is split.

5. The brim of claim 1 or 2 wherein said contact surfaces are of an enlarged thickness to provide said support.

6. The apparatus of claims 1, 2 or 3 wherein said brim is molded of a material selected from the group consisting of polyethylene and polyurethane foam.

* * * * *